(12) United States Patent
Xu et al.

(10) Patent No.: US 9,937,027 B2
(45) Date of Patent: Apr. 10, 2018

(54) ELECTRIC TOOTHBRUSH

(71) Applicant: HANGZHOU NEWLY TECHNOLOGY CO., LTD, Zhejiang (CN)

(72) Inventors: Xiaoping Xu, Zhejiang (CN); Shiwei Shen, Zhejiang (CN)

(73) Assignee: HANGZHOU NEWLY TECHNOLOGY CO., LTD., West Lake Hangzhou, Zhejiang (CN)

( * ) Notice: Subject to any disclaimer, the term of this patent is extended or adjusted under 35 U.S.C. 154(b) by 419 days.

(21) Appl. No.: 14/424,888

(22) PCT Filed: Nov. 27, 2013

(86) PCT No.: PCT/CN2013/087981
§ 371 (c)(1),
(2) Date: Feb. 27, 2015

(87) PCT Pub. No.: WO2014/082579
PCT Pub. Date: Jun. 5, 2014

(65) Prior Publication Data
US 2015/0223919 A1 Aug. 13, 2015

(30) Foreign Application Priority Data
Nov. 30, 2012 (CN) .......................... 2012 1 0502534

(51) Int. Cl.
*A61C 17/26* (2006.01)
*A46B 9/04* (2006.01)
*A61C 17/22* (2006.01)

(52) U.S. Cl.
CPC .............. *A61C 17/26* (2013.01); *A46B 9/045* (2013.01); *A61C 17/222* (2013.01)

(58) Field of Classification Search
CPC ......... A46B 13/02; A46B 9/045; A61C 17/22; A61C 17/24; A61C 17/26
(Continued)

(56) References Cited

U.S. PATENT DOCUMENTS 1,225,955 A * 5/1917 Hickman ...................... 15/167.2
1,911,973 A * 5/1933 Ruse ....................... A46B 9/045
15/167.2

(Continued)

FOREIGN PATENT DOCUMENTS

CN 2699852 Y 5/2005
CN 2788761 Y 6/2006
(Continued)

OTHER PUBLICATIONS

Partial machine translation of WO 97/34545, Sep. 25, 1997.*
International Search Report in International Application No. PCT/CN2013/087981, filed Nov. 27, 2013.

*Primary Examiner* — Mark Spisich
(74) *Attorney, Agent, or Firm* — Saliwanchik, Lloyd & Eisenschenk

(57) ABSTRACT

An electric toothbrush comprises a toothbrush handle (1), a toothbrush rod (2) and a toothbrush head. The toothbrush head comprises a left-rotating hairbrush and a right-rotating hairbrush (3, 3'), which are oppositely and rotatably fixed on a toothbrush shaft (4). The right end of the toothbrush shall (4) is arranged in a shaft hole at the upper end of the toothbrush rod (2) and is axially positioned on the shaft hole through the right-rotating hairbrush (3') and a shaft cap arranged at the right end of the toothbrush shaft (4); and the bristles of each of the left-rotating hairbrush and the right-rotating hairbrush (3, 3') comprise an inner ring of bristles and an outer ring of bristles (6, 6', 7, 7').

8 Claims, 5 Drawing Sheets

(58) Field of Classification Search
USPC .......................................... 15/22.1, 28, 167.2
See application file for complete search history.

(56) References Cited

U.S. PATENT DOCUMENTS

| | | | | |
|---|---|---|---|---|
| 2,306,264 A | * | 12/1942 | Hart | .......................... A46B 7/08 |
| | | | | 15/167.2 |
| 3,732,589 A | * | 5/1973 | Burki | ..................... A61C 17/26 |
| | | | | 15/167.2 |
| 5,177,826 A | | 1/1993 | Vrignaud et al. | |
| 7,832,043 B1 | | 11/2010 | Feldman | |
| 2008/0052845 A1 | | 3/2008 | Djang | |

FOREIGN PATENT DOCUMENTS

| | | | |
|---|---|---|---|
| CN | 201492532 U | | 6/2010 |
| CN | 102793591 A | | 11/2012 |
| CN | 102920520 A | | 2/2013 |
| CN | 203059956 U | | 7/2013 |
| DE | 20317780 U1 | | 2/2004 |
| WO | WO-8901303 A1 | | 2/1989 |
| WO | 97/34545 | * | 9/1997 |

* cited by examiner

ELECTRIC TOOTHBRUSH

BACKGROUND OF THE INVENTION

1. Field of the Invention

The present invention relates to toothbrushes, particularly an electric toothbrush able to clean the tooth in a full range.

2. Description of the Related Art

Heretofore, toothbrush has become an essential everyday items. There are varieties of toothbrush. Electric toothbrush is very convenient for people to brush. However, there are too many defects in conventional electric toothbrush making electric toothbrush unpopular.

U.S. Pat. No. 3,732,589 discloses an electric toothbrush. The brush head of the patent consists of mainly by left rotating brush and right rotating brush which are set oppositely, the said two rotating brushes are connected by a pipe as a whole. The outer wall of the pipe also has bristles. The brush shaft pass through the inner hole of the pipe. One end of the brush shaft is fixed to the tip of the brush rod. Electric toothbrush with this structure is able to simultaneously scrub blade of upper teeth and blade of lower teeth and teeth itself. Thus improving the efficiency of brushing. However, the solution of this patent still has the following defects: the volume of the brush head is too big because of the structure it has. This defect causes not only a waste of material, but also an inconvenience for the brush head to move in the mouth and a uncomfortable feeling. Brushing effect is affected.

SUMMARY OF THE INVENTION

The prevent invention has been devised in order to solve the problem described above, and will provide a electrical tooth brush with simple structure in small size, and being easy to move in the mouth.

To achieve the above object, the present invention may take the following technical solution:

As the first aspect of the present invention, an electric toothbrush comprises a toothbrush handle 1, a toothbrush rod 2 and a toothbrush head; the toothbrush head consists of a left-rotating hairbrush and a right-rotating hairbrush 3, 3', which are oppositely and rotatably fixed on a toothbrush shaft 4; the right end of the toothbrush shaft 4 is arranged in a shaft hole at the upper end of the toothbrush rod 2 and is axially positioned on the shaft hole through the right-rotating hairbrush 3' and a shaft cap 41 arranged at the right end of the toothbrush shaft 4; a power source in the toothbrush handle 1 is in driving connection with a gear 11, and the gear 11 mesh the gear 31' at the right side of the right-rotating hairbrush 3' through a driving shaft 5 in the toothbrush rod 2; and the bristles of each of the left-rotating hairbrush and the right-rotating hairbrush 3, 3' consists of an inner ring of bristles and an outer ring of bristles 6, 6', 7, 7';

the appropriate distance A between the ends of Left outer ring of bristles 7 and the ends of right outer ring of bristles 7' is equivalent to or less than the thickness of tooth;

the ends of the left inner ring of bristles 6 overlap the ends of the right inner ring of bristles 6', or there is a gap B lessen than the distance A between the ends of left inner ring of bristles 6 and the ends of right inner ring of bristles 6';

left or right inner ring of bristles 6, 6' parallel to the axis of the brush axis 4 or constitute a smaller angle M with the axis of the brush axis 4;

left or right outer ring of bristles 7, 7' and the axis of the brush shaft 4 constitute a larger angle N.

Thus according to the first aspect of the present invention, the distance A is 0.5-5 mm, the gap B is 0-3 mm, M is an angle of 0-15 degree, N is an angle of 15-70 degree.

Preferably, M is an angle of 6 degree, N is an angle of 35 degree, the distance A is 3 mm, the gap B is 0 mm.

In the aspect described above, the length of the left inner ring of bristles 6 overlapping the right inner ring of bristles 6' along the axis is 1 mm.

In the aspect described above, the power source is consisted of gear motor 8 and battery 9, and a connector 10 is set between the gear motor 8 and the driving shaft 5.

Advantage of the invention compared to the prior art.

In the technical solution of the invention, the toothbrush head consists of a left-rotating hairbrush and a right-rotating hairbrush, which are oppositely and rotatably fixed on a toothbrush shaft. By this structure, brush shaft can directly drive left-rotating hairbrush and a right-rotating hairbrush. Thus, the advantage of simple structure is achieved.

The right end of the toothbrush shaft is arranged in a shaft hole at the upper end of the toothbrush rod and is axially positioned on the shaft hole through the right-rotating hairbrush and a shaft cap arranged at the right end of the toothbrush shaft. By this structure, the transmission structure of the top of brush drive rod is simplified, and the size of the top of brush rod is reduced.

The bristles of the left-rotating hairbrush or the right-rotating hairbrush consists of an inner ring of bristles and an outer ring of bristles; Left or right inner ring of bristles parallel to the axis of the brush axis or constitutes a smaller angle M (0-15 degree) with the axis of the brush axis; the ends of the left inner ring of bristles interlace the ends of the right inner ring of bristles, or there is a gap B (0-3 mm) lessen than the distance A between the left inner ring of bristles and the right inner ring of bristles. By this structure, the bristles of the left-rotating hairbrush and the right-rotating hairbrush are able to simultaneously scrub blade of upper teeth and blade of lower teeth. Driven by the centrifugal force, the tips of the bristles of left-rotating hairbrush and the right-rotating hairbrush left rise, thus the tips can also brush the blade of the upper and lower teeth. Compared with the prior art of U.S. Pat. No. 3,732,589, the invention takes the advantage that the intermediate pipe is omitted. Thus the radial size of brush head is significantly reduced. This change causes the advantage that material is saved, and the discomfort feeling when the brush head moves in the mouth is relieved, and it becomes easy for the brush head to move in the mouth. Brushing effect is improved.

Left or right outer ring of bristles and the axis of the brush shaft constitute a larger angle N (15-70 degree). The appropriate distance A between the ends of Left outer ring of bristles and the ends of right outer ring of bristles is equivalent to or less than the thickness of tooth. By this structure, by rotating left and right outer ring of bristles, the inside and the outside of the teeth are brushed top-down or bottom-up or from left to right. Compared with the prior art, the outer ring of bristles of the invention needs only a single layer of bristles bringing the advantage of saving bristles, and simplifying the structure, and reducing the weight.

DETAILED DESCRIPTION OF THE INVENTION

Herebelow, embodiment of the present invention will be described in detail with reference to the drawings.

Figure 1:
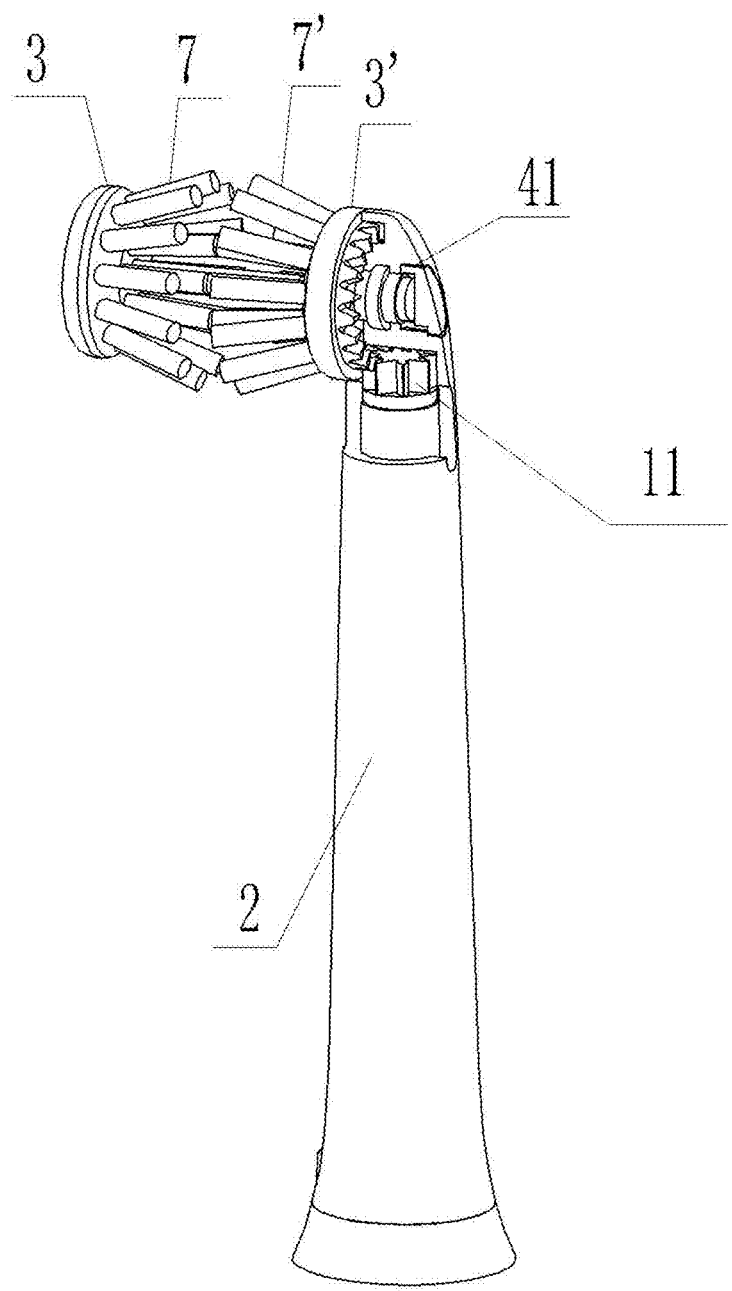
FIG. 1 is a (partially sectional) plan view of overall structure of the present invention.
Figure 1A:
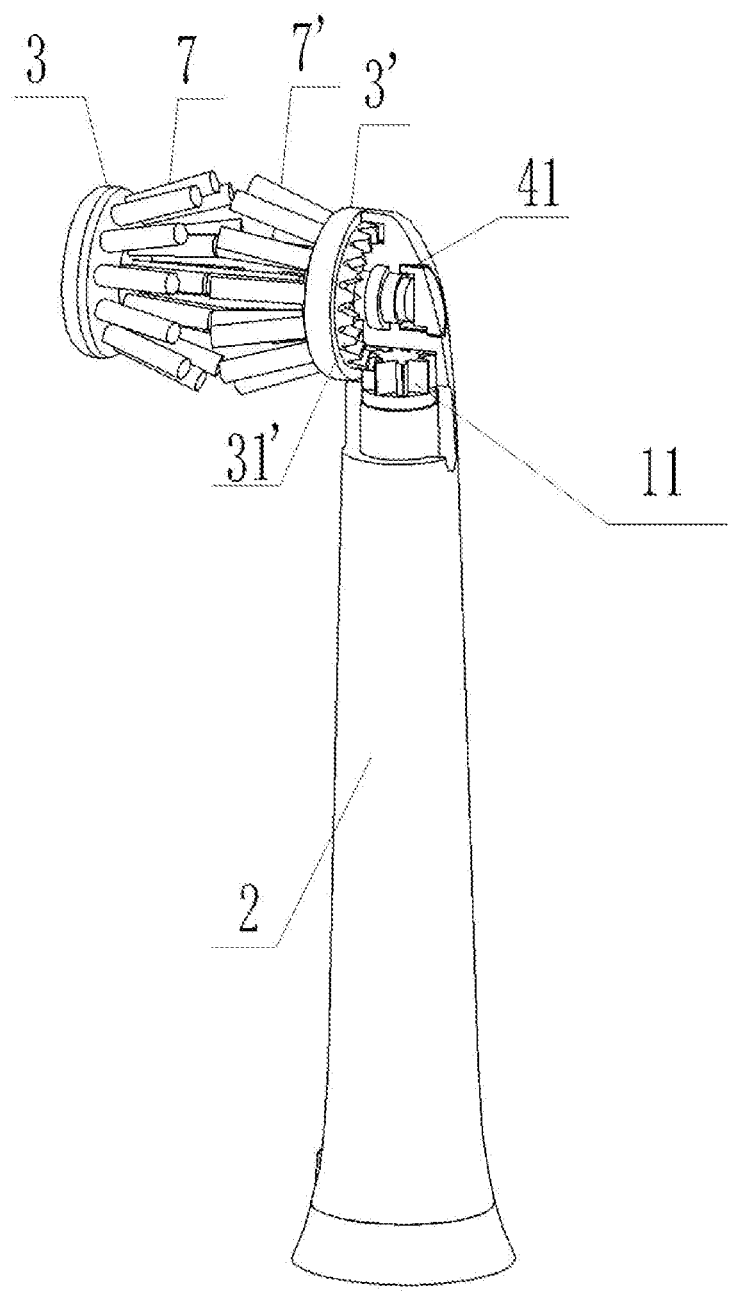
FIG. 1a is an exploded view of structure of the present invention.
Figure 2:
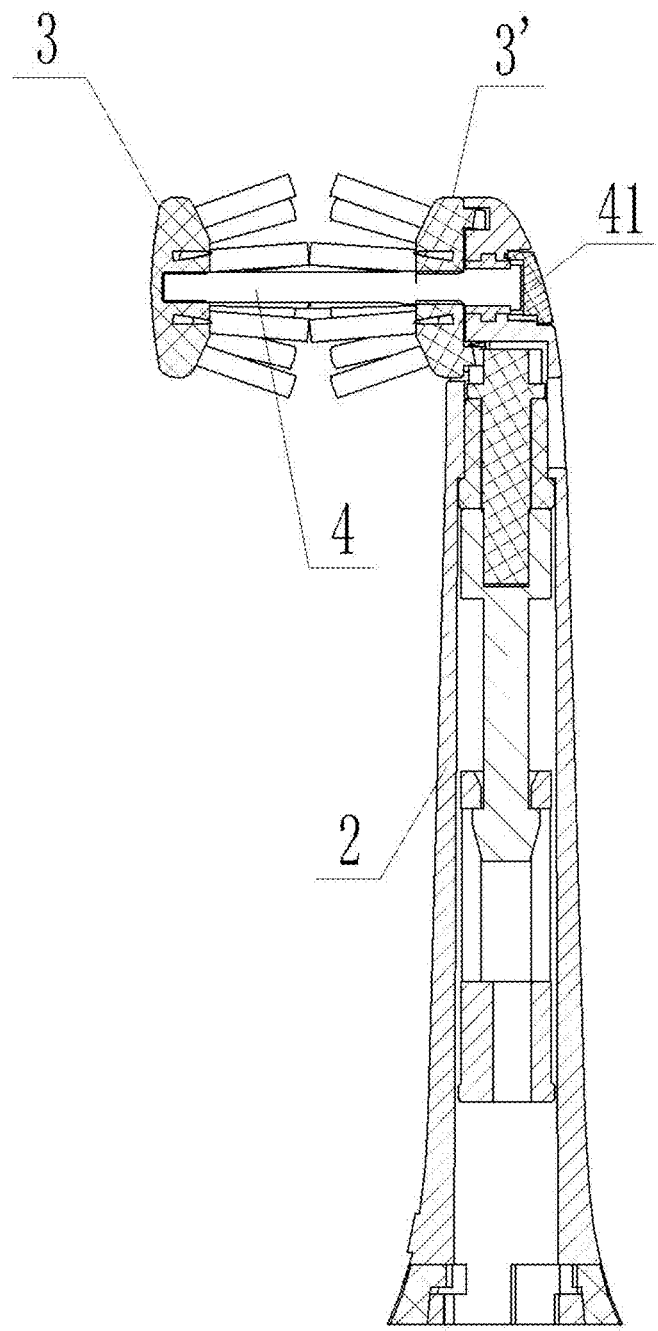
FIG. 2 is a view showing components of the present invention.
Figure 3:
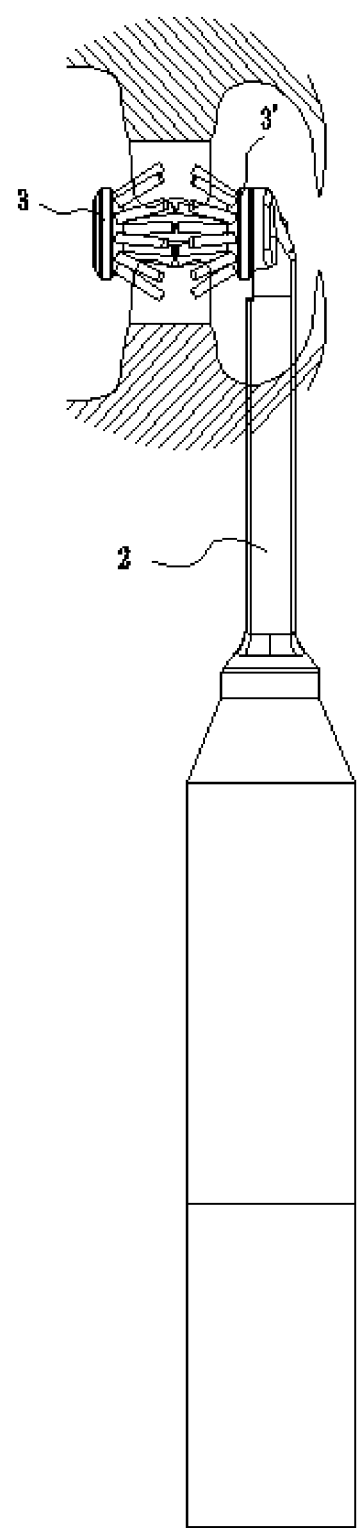
FIG. 3 is a schematic view of a state of use of the present invention.
Figure 4:
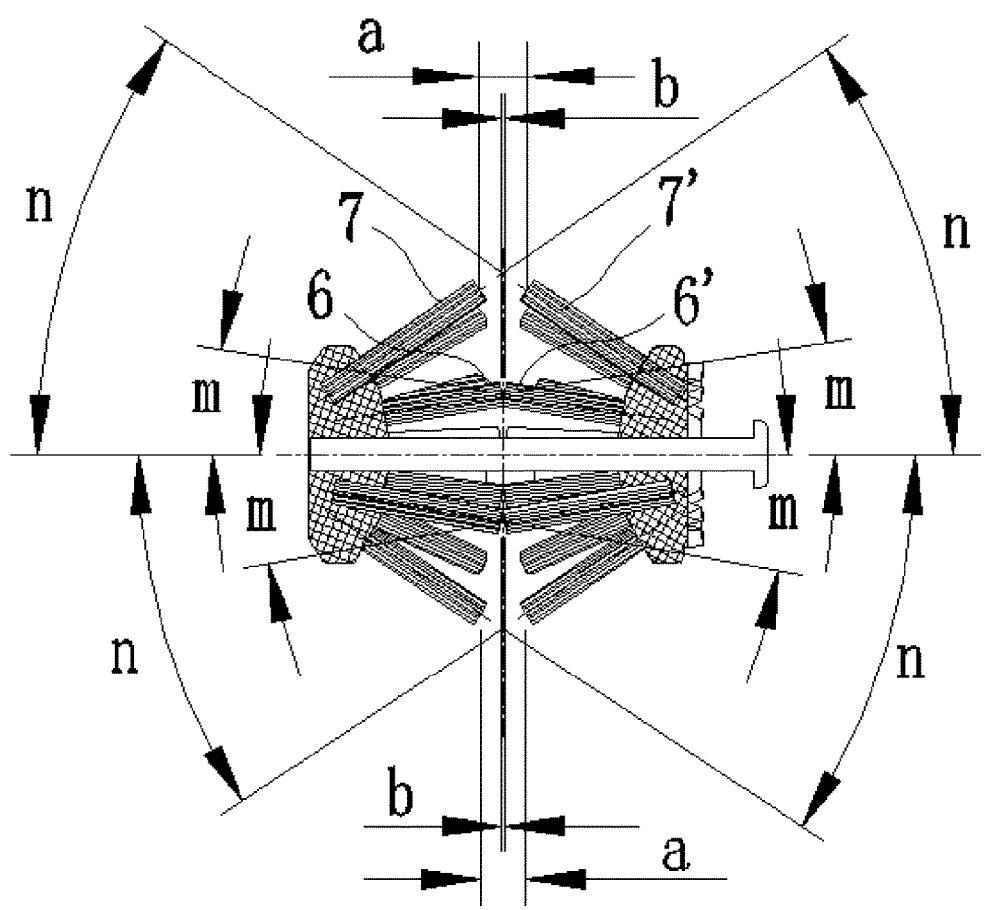
FIG. 4 is a schematic view of labelled rotary brush of FIG. 1.

First, overall structure of an electric toothbrush relating to the present embodiment will be described with reference to FIG. 1 to FIG. 4.

An electric toothbrush comprises a toothbrush handle 1, a toothbrush rod 2 and a toothbrush head. The toothbrush head consists of a left-rotating hairbrush and a right-rotating hairbrush 3, 3', which are oppositely and rotatably fixed on a toothbrush shaft 4. The right end of the toothbrush shaft 4 is arranged in a shaft hole at the upper end of the toothbrush rod 2 and is axially positioned on the shaft hole through the right-rotating hairbrush 3' and a shaft cap 41 arranged at the right end of the toothbrush shaft 4; a power source in the toothbrush handle 1 is in driving connection with a gear 11, and the gear 11 mesh the gear 31' at the right side of the right-rotating hairbrush 3' through a driving shaft 5 in the toothbrush rod 2; and the bristles of each the left-rotating hairbrush and the right-rotating hairbrush 3, 3' consists of an inner ring of bristles and an outer ring of bristles 6, 6', 7, 7'.

The said power source is a gear motor 8 powered by a battery 9 fixed in the toothbrush handle 1. The gear motor 8 coupled with the low end of the driving shaft 5 through connector 10 in the toothbrush rod 2. The up end of the driving shaft 5 is coupled with a gear 11, and the gear 11 mesh the gear 31' at the right side of the right-rotating hairbrush 3'.

The appropriate distance a between the ends of Left outer ring of bristles 7 and the ends of right outer ring of bristles 7' is equivalent to or less than the thickness of tooth. Preferably distance A is in the range of 0.5~5 mm according to the different races. The most preferably, the distance A is 3 mm.

There is a gap B lessen than the distance a between the ends of left inner ring of bristles 6 and the ends of right inner ring of bristles 6'. Preferably the gap B is in the range of 0~3 mm according to the different races. The most preferably, the gap B is 0 mm. The ends of the left inner ring of bristles 6 interlace the ends of the right inner ring of bristles 6'.

Alternatively, left inner ring of bristles 6 and right inner ring of bristles 6' overlap along the axis of the toothbrush shaft 4. Preferably, the length that left inner ring of bristles 6 overlap right inner ring of bristles 6' is 1 mm.

Left inner ring of bristles 6 and right inner ring of bristles 6' parallel to the axis of the toothbrush shaft 4, or each of them constitutes a smaller angle M with the axis of the toothbrush shaft 4. Preferably, M is an angle of 6 degree.

Left outer ring of bristles 7 or right outer ring of bristles 7' constitutes an angle N with the axis of the brush shaft 4. Most preferably, N is an angle of 35 degree.

The invention claimed is:

1. An electric toothbrush comprising: a toothbrush handle (1), a toothbrush rod (2) and a toothbrush head; the toothbrush head comprises a left-rotating hairbrush and a right-rotating hairbrush (3, 3'), which are oppositely and rotatably fixed on a toothbrush shaft (4); the right end of the toothbrush shaft (4) is arranged in a shaft hole at the upper end of the toothbrush rod (2) and is axially positioned on the shaft hole through the right-rotating hairbrush (3') and a shaft cap arranged at the right end of the toothbrush shaft (4); a power source in the toothbrush handle (1) is in driving connection with a gear (11) at the right side of the right-rotating hairbrush (3') through a driving shaft (5) in the toothbrush rod (2); and the bristles of each of the left-rotating hairbrush and the right-rotating hairbrush (3, 3') comprise an inner ring of bristles and an outer ring of bristles (6, 6', 7, 7');

wherein an appropriate distance A separates the ends of left outer ring of bristles (7) and the ends of right outer ring of bristles (7');

wherein the ends of the left inner ring of bristles (6) overlap the ends of the right inner ring of bristles (6'), or there is a gap B between the ends of left inner ring of bristles (6) and the ends of right inner ring of bristles (6') that is less than the distance A;

wherein the left or right inner ring of bristles (6, 6') is parallel to the axis of the toothbrush shaft (4) or constitutes an angle M with the axis of the toothbrush shaft (4); and wherein the left or right outer ring of bristles (7, 7') and the axis of the toothbrush shaft (4) constitutes an angle N that is larger than angle M.

2. The electric toothbrush according to claim 1, wherein: the distance A is 0.5-5 mm, the gap B is 0-3 mm, M is an angle of 0-15 degree, and N is an angle of 15-70 degree.

3. The electric toothbrush according to claim 2, wherein: M is an angle of 6 degree, N is an angle of 35 degree, the distance A is 3 mm, and the gap B is 0 mm.

4. The electric toothbrush according to claim 3, wherein: the power source comprises a gear motor (8) and battery (9), and a connector (10) is set between the gear motor (8) and the driving shaft (5).

5. The electric toothbrush according to claim 2, wherein: the power source comprises a gear motor (8) and battery (9), and a connector (10) is set between the gear motor (8) and the driving shaft (5).

6. The electric toothbrush according to claim 1, wherein: the length of the left inner ring of bristles (6) overlapping the right inner ring of bristles (6') along the axis is 1 mm.

7. The electric toothbrush according to claim 6, wherein: the power source comprises a gear motor (8) and battery (9), and a connector (10) is set between the gear motor (8) and the driving shaft (5).

8. The electric toothbrush according to claim 1, wherein: the power source comprises a gear motor (8) and battery (9), and a connector (10) is set between the gear motor (8) and the driving shaft (5).

* * * * *